US010027215B2

(12) United States Patent
Wieters

(10) Patent No.: US 10,027,215 B2
(45) Date of Patent: Jul. 17, 2018

(54) BISTABLE ELECTROMAGNETIC ACTUATOR AND SURGICAL INSTRUMENT

(71) Applicant: OLYMPUS WINTER & IBE GMBH, Hamburg (DE)

(72) Inventor: Martin Wieters, Barsbuettel (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 15/265,250

(22) Filed: Sep. 14, 2016

(65) Prior Publication Data

US 2017/0005557 A1 Jan. 5, 2017

Related U.S. Application Data

(63) Continuation of application No. PCT/EP2015/054539, filed on Mar. 4, 2015.

(30) Foreign Application Priority Data

Mar. 14, 2014 (DE) .................. 10 2014 204 736

(51) Int. Cl.
*H02K 41/03* (2006.01)
*H02K 33/16* (2006.01)
(Continued)

(52) U.S. Cl.
CPC ....... *H02K 41/035* (2013.01); *A61B 1/00158* (2013.01); *H01F 7/1615* (2013.01);
(Continued)

(58) Field of Classification Search
CPC ......... H02K 33/00–33/18; H02K 35/00–35/06
(Continued)

(56) References Cited

U.S. PATENT DOCUMENTS 3,103,603 A * 9/1963 Reutter .................. H02K 26/00
310/15
4,023,056 A * 5/1977 Yamada .............. B60R 21/0136
280/735
(Continued)

FOREIGN PATENT DOCUMENTS

CN 103026429 A 4/2013
DE 1464249 A1 2/1969
(Continued)

OTHER PUBLICATIONS

Machine Translation, Nestler et al., DE 102012104832 A1, Dec. 2013.*
(Continued)

*Primary Examiner* — Thomas Truong
(74) *Attorney, Agent, or Firm* — Scully, Scott, Murphy & Presser, P.C.

(57) ABSTRACT

A bistable electromagnetic actuator including: a tube; a stator arranged outside of the tube; and a rotor mounted in the tube so as to be displaceable along the longitudinal axis, the rotor at least partially comprises one or more of a paramagnetic and a ferromagnetic material and can be reversibly displaced between a first position and a second position by applying an electromagnetic field; wherein the stator comprises two ring permanent magnets, a coil for producing the electromagnetic field, and a back-iron element having two stator pole shoes; and the two ring permanent magnets comprise hard magnetic particles that are embedded in a plastic matrix.

11 Claims, 1 Drawing Sheet

(51) Int. Cl.
  *H02K 21/38* (2006.01)
  *H02K 3/50* (2006.01)
  *H02K 41/035* (2006.01)
  *H01F 7/16* (2006.01)
  *H01F 41/02* (2006.01)
  *A61B 1/00* (2006.01)
  *H01F 1/08* (2006.01)
  *A61B 34/00* (2016.01)

(52) U.S. Cl.
  CPC ........... *H01F 41/0266* (2013.01); *H02K 3/50* (2013.01); *H02K 21/38* (2013.01); *H02K 33/16* (2013.01); *A61B 1/00096* (2013.01); *A61B 2034/731* (2016.02); *H01F 1/083* (2013.01); *H01F 2007/1669* (2013.01)

(58) Field of Classification Search
  USPC ............ 310/15–39, 12.04, 71; 335/266, 229
  See application file for complete search history.

(56) References Cited

U.S. PATENT DOCUMENTS

| | | | | |
|---|---|---|---|---|
| 4,127,835 A * | 11/1978 | Knutson | ............... | H01F 7/1615 310/30 |
| 4,315,197 A | 2/1982 | Studer | | |
| 8,264,104 B2 | 9/2012 | Schrader | | |
| 9,385,580 B2 | 7/2016 | Wieters et al. | | |
| 2010/0264758 A1 | 10/2010 | Strohm et al. | | |
| 2013/0193778 A1* | 8/2013 | Wieters | .............. | A61B 1/00133 310/12.04 |
| 2016/0115960 A1* | 4/2016 | Fournier | ................... | F01P 5/14 123/41.44 |

FOREIGN PATENT DOCUMENTS

| | | | | |
|---|---|---|---|---|
| DE | 102008042701 A1 | | 4/2010 | |
| DE | 102011006814 A1 | | 1/2012 | |
| DE | 102012104832 A1 * | | 12/2013 | ........... H01F 7/1615 |
| FR | 2929753 A1 | | 10/2009 | |
| JP | S50-085041 A | | 7/1975 | |
| JP | H10-027361 A | | 1/1998 | |
| JP | 2004-153907 A | | 5/2004 | |
| JP | 2013-530672 A | | 7/2013 | |
| WO | WO 2014/121881 A1 | | 8/2014 | |
| WO | WO 2014198326 A1 * | | 12/2014 | ................ F01P 5/14 |

OTHER PUBLICATIONS

International Search Report dated Nov. 20, 2015 issued in PCT/EP2015/054539.

Dipl.-Ing Philipp Abel: "Miniaturisierte Aktuatoren für die Umsetzung optischer Funktionalitäten in medizinischen Videoendoskopen, Doktoringenieur (Dr.Ing.)" 2012, XP 055206707.

Diplom-Ingenieur et al: "Elektromechanische and optische Systeme für die Endoskopie", Berlin, 2011, p. 83, XP 055206502.

GW Reppel: "Duroplastgepresste Magnete—Werkstoffe, Verfahren und Eigenschaften", 2004, XP 055206743.

Chinese Office Action dated Jan. 29, 2018 in Chinese Patent Application No. 201580010883.7.

Japanese Office Action dated Jan. 23, 2018 in Japanese Patent Application No. 2016-557299.

* cited by examiner

BISTABLE ELECTROMAGNETIC ACTUATOR AND SURGICAL INSTRUMENT

CROSS-REFERENCE TO RELATED APPLICATION

The present application is a continuation of PCT/EP2015/054539 filed on Mar. 4, 2015, which is based upon and claims the benefit to DE 10 2014 204 736.6 filed on Mar. 14, 2014, the entire contents of each of which are incorporated herein by reference.

BACKGROUND

Field

The present application relates to a bistable electromagnetic actuator, such as for use in a surgical instrument, comprising a stator arranged outside of a tube, and a rotor mounted in the tube so as to be displaceable along the longitudinal axis, the rotor at least partially comprises a paramagnetic and/or ferromagnetic material and can be reversibly displaced between a first position and a second position by applying an electromagnetic field, wherein the stator comprises two, which can be oppositely axially poled, ring permanent magnets, a coil for producing the electromagnetic field, and a back-iron element having two stator pole shoes; as well as a surgical instrument.

Prior Art

Bistable electromagnetic actuators have a rotor that is held in one of two extreme positions in a permanent magnetic field, and can be moved out of one stable position into the other stable position by switching an electromagnetic field. This can for example actuate switches. In the case of surgical instruments, such as endoscopes, these compact actuators can be used for example to change a focus or enlarge an optical system, or to change a direction of viewing. This is accomplished in that an optical component is moved by the actuator, wherein the optical component is located in or on the rotor of the actuator.

A linear motor for optical systems such as endoscopes is known from DE 10 2008 042 701 A1. The motor has a stator with two permanent magnets which are polled in the same direction and magnetically connected to each other with a back-iron element. A coil is arranged between the magnets. On the side next to each magnet, a pole shoe is magnetically connected to the back-iron element. The motor rotor comprises a yoke consisting of a soft magnetic material that magnetically engages with the permanent magnet of the stator. By supplying current to the coil, the rotor can be moved in the longitudinal direction from a resting position.

The rotor according to DE 10 2008 042 701 A1 consists of a tubular, soft magnetic element so that a strong force must be expended to move the rotor from one position into the other position due to the resulting friction of the tubular rotor against the tube. Furthermore, the linear motor according to DE 10 2008 042 701 A1 is comparatively large.

Conventional actuators use permanent magnets that can also be designated permanent magnet rings, for example consisting of magnetic materials such as NdFeB or SmCo. These magnetic materials are brittle and therefore very sensitive to mechanical loads. With endoscopes, it is additionally desirable to use minute magnets and small outer diameters. This makes the production of the ring permanent magnet very involved. In addition, the ring permanent magnets are very easy to damage when being installed and must be specially protected even in an installed state to prevent damage.

Furthermore, it is important to use two ring permanent magnets that only have a minor dimensional deviation from each other since otherwise an excessive deviation in symmetry can arise in the actuator which for example can produce malfunctioning or poor functioning of the actuator. For example in one of the bistable positions, less holding force can arise on one side than in the other bistable position, which may not be desirable. This can be avoided by sorting conventional ring permanent magnets into pairs that, for example, are manufactured by sintering and then ground to size in order for example to install if possible magnets with the same dimensions and the same magnetic properties in an endoscope.

SUMMARY

It is an object to provide a compact bistable electromagnetic actuator and a surgical instrument with a correspondingly bistable electromagnetic actuator that are produced economically and enable symmetrical forces in both bistable positions.

Such object can be achieved with a bistable electromagnetic actuator, such as for use in a surgical instrument, comprising a stator arranged outside of a tube, and a rotor mounted in the tube so as to be displaceable along the longitudinal axis, which rotor at least partially comprises a paramagnetic and/or ferromagnetic material and can be reversibly displaced between a first position and a second position by applying an electromagnetic field, wherein the stator comprises two, which can be oppositely axially poled, ring permanent magnets, a coil for producing the electromagnetic field, and a back-iron element having two stator pole shoes, the ring permanent magnets comprising magnetic particles that are embedded in a plastic matrix.

Through the use of ring permanent magnets which comprise hard magnetic particles embedded in a plastic matrix, very precise production of ring permanent magnets is enabled. The ring permanent magnets can consist of hard magnetic particles embedded in a plastic matrix.

The ring permanent magnets can be produced in a batch, such as by means of an injection molding procedure, and can be produced with only very slight structural deviations since they are produced using the same process parameters. Nearly identical ring permanent magnets are therefore producible within a lot of manufactured ring permanent magnets. Furthermore, such ring permanent magnets that are manufactured from a compound of a polymer material and magnetic particles possess better mechanical properties. These are namely less brittle than corresponding magnets consisting of the solid material.

Furthermore, the magnets can also be very efficiently and economically manufactured in large quantities through a corresponding injection molding technique. The hard magnetic particles can consist of NdFeB or SmCo. Furthermore, the plastic matrix can consist of a polymer. The plastic matrix can have a polyphenylene sulfide (PPS), or respectively consist thereof. This is a high-temperature-resistant thermoplastic plastic. As an alternative, a polyamide such as a polyamide 12 can be used.

The ring permanent magnets can be manufactured in an injection molding method. The ring permanent magnets can be injection molded with any geometry and subsequently also magnetized.

An opening or passage penetrating the ring permanent magnet in a longitudinally axial direction for at least one coil wire of the coil can be provided in at least one ring permanent magnet. This allows the bistable electromagnetic actuator to be produced with a very small diameter since feeding the at least one coil wire around the ring permanent magnet, i.e., either from the outside or from the inside of the coil wire to the coil, is avoided.

With such embodiment of the bistable electromagnetic actuator, it is possible to provide a very symmetrical configuration of the ring permanent magnet by using two ring permanent magnets which each have an opening or passage for at least one coil wire of the coil that penetrates the ring material in the longitudinal axial direction. The weakening of the magnet is then namely symmetrical. In this case, however, only one opening or penetration in a magnet must serve to accommodate a coil wire of the coil. It is unnecessary for the opening or penetration to be provided with a coil wire of the coil in the other ring permanent magnet.

An opening or passage penetrating the stator pole shoe in a longitudinally axial direction for at least one coil wire of the coil can be provided in at least one stator pole shoe. The coil wire of the coil may thereby be guided through a stator pole shoe as well as through a ring permanent magnet. Both stator pole shoes can have an opening or passage that runs through the stator pole shoe in the longitudinal axial direction.

In the embodiments in which both ring permanent magnets and/or both stator pole shoes have an opening or passage for at least one coil wire of the coil, the opening or passage can be flush in a longitudinal direction with the respective opening or passage of the other ring permanent magnet and/or with the other stator pole shoe.

The outer diameter of the ring permanent magnets can be less than or equal to 5 mm, such as being less than 3 mm and less than 2.5 mm. The wall thickness of the ring permanent magnets, i.e., in the radial and/or axial direction, can be less than 0.6 mm, such as being less than 0.4 mm and less than 0.3 mm. The ring permanent magnets can be each arranged on one side of the coil.

The back-iron element with the stator pole shoes can comprise the coil, and the stator pole shoes can be arranged on both sides of the coil between the coil and the ring permanent magnets, wherein the rotors have two rotor pole shoes, wherein one axial width of the stator pole shoes can be less than one axial width of the rotor pole shoes.

The coil current and power loss in the coil can thereby be minimized by increasing the efficiency of the coil. This can be achieved by the geometry of the actuator elements. The geometry can result from the fact that the back-iron element with the stator pole shoe no longer encloses both the coil and ring magnets as disclosed in DE 10 2008 042 701 A1, but only encloses the coil and the ring magnets are arranged outside of the stator pole shoes. Axially magnetized magnetic rings can be used for this purpose since a radially-arranged soft iron of the back-iron element is not needed on the magnetic rings. For this reason, the stator can be realized in a smaller radial installation space. Since the stator pole shoes are arranged between the permanent magnets and coil, a greater coil efficiency results since the pole shoes are connected directly to the back iron. The axial length of the stator and hence the axial length of the rotor as well can thereby be reduced.

Since the rotor itself has rotor pole shoes, it has a central, radial tapering, and a pole shoe is therefore formed on each of its ends. The rotor therefore only contacts the tube at the locations of the pole shoes and no longer the entire surface. Accordingly, the friction can be reduced between the rotor and the tube in which the rotor is arranged. This increases the switching efficiency since less friction resistance must be overcome. In addition, the negative influence of, for example, straightness errors or curves are reduced due to the smaller fit that is decreased to two small contact surfaces, or respectively contact lines.

Overall, this yields a favorable efficiency of the coil, or respectively actuator, and an effective balance between holding force and switching force.

If the axial width of the stator pole shoes is less than an axial stroke of the actuator between the first position and the second position, major differences between the holding force and switching force can be achieved.

The rotor with the rotor pole shoes can possess an overall length in the axial direction that is greater than the outer distance between the stator pole shoes in an axial direction. A distance between the axial middle planes of the rotor pole shoes can be greater than a distance between the axial middle planes of the stator pole shoes. Due to such features, the balance between the holding force and switching force can be easily adjusted, and the switching force can be increased.

When the stator pole shoes have the same axial width between each other, and/or the rotor pole shoes have the same axial width between each other, and/or the stator(s) and/or the rotor(s) is/are formed symmetrically across a plane of symmetry, a symmetrical actuator structure is realized in an axial direction such that, in the two end positions, or respectfully in the first position and the second position, the same holding forces predominate and the same switching forces are used for changing the position of the rotor in the actuator. In addition, only some of the cited geometric dimensions can be designed symmetrical. When the actuator is subjected to a constant load during operation, for example from one side, it can be possible to brake up the overall symmetry of the actuator in an axial direction and effectuate greater holding force and/or switching force in one position than in the other position.

The rotor can lie against a stop in the first and/or second position. The stop can be arranged such that the force exerted on the rotor in this position by the permanent magnets presses or draws the rotor toward the stop against which the rotor lies.

In one development in an end position, such as the first or second position, the rotor pole shoe can be arranged at the end position to at least partially cover in an axial direction the stator pole shoe opposite the rotor pole shoe, wherein a middle plane of the rotor pole shoe arranged at the end position can be arranged beyond a middle plane of the stator pole shoe opposite the rotor pole shoe in an axial direction toward the end position. This concerns the rotor pole shoe, or respectively stator pole shoe, that is arranged closer to the momentary end position in an axial direction. In the case on an endoscope, this would be the distal pole shoes of the stator and rotor in the distal end position. These lie opposite each other. In the proximal end position, these are the proximal pole shoes of the stator and rotor. These also lie opposite each other.

An end position for the rotor pole shoe not arranged at the end position can at least partially cover in an axial direction the stator pole shoe opposite the rotor pole shoe, wherein a middle plane of the rotor pole shoe not arranged at the end position can be arranged beyond a middle plane of the stator pole shoe opposite the rotor pole shoe in an axial direction toward the end position. In an endoscope, these can be the proximal pole shoes of the rotor and stator, and vice versa, in the distal end position of the rotor.

These two configurations, individually or together, mean that very stable and strong holding force can be realized with little effort when current is supplied to the coil in the respective end position due to the favorable conduction of the magnetic flux. In addition, the switching force acting on the rotors is significantly increased.

Finally, a surgical instrument, such as an endoscope, is also provided having the above-described bistable electromagnetic actuator. Since the actuator can be built very small, it can also be implemented in an endoscope having a narrow endoscope shaft.

Further features will become apparent from the description of embodiments together with the claims and the included drawings. Embodiments can fulfill individual characteristics or a combination of several characteristics.

BRIEF DESCRIPTION OF THE DRAWINGS

The embodiments are described below, without restricting the general concept, using exemplary embodiments with reference to the drawings, wherein we expressly refer to the drawings with regard to all details that are not explained in greater detail in the text. In the figures.

In the drawings, the same or similar types of elements and/or parts are provided with the same reference numbers so that a re-introduction is omitted.

DETAILED DESCRIPTION

Figure 1:
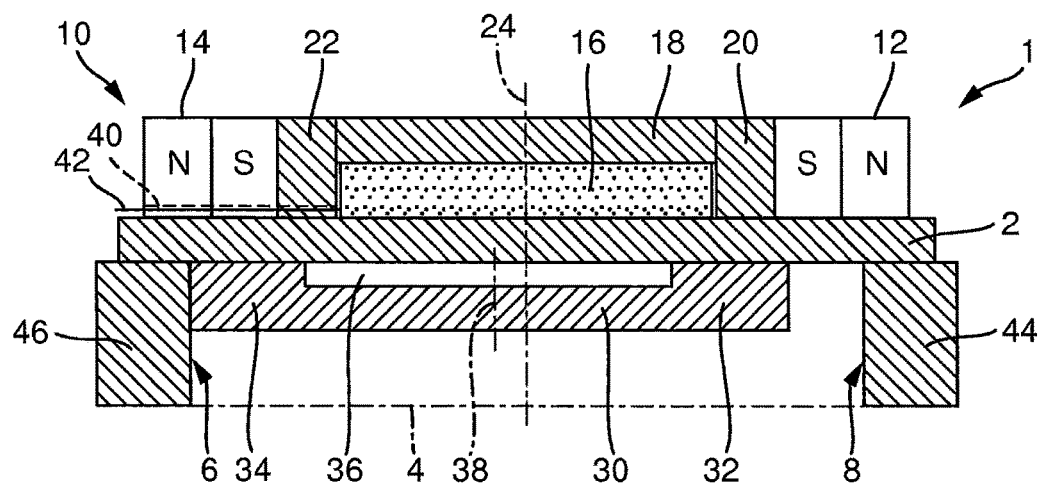
FIG. 1 illustrates a schematic cross-sectional view of an actuator.

FIG. 1 shows a cross-section of a bistable electromagnetic actuator 1. The actuator 1 is substantially rotationally symmetrical about the central axis 4 and only one-half of the actuator 1 is depicted. The entire section of the actuator 1 results from mirroring across the central axis 4.

In the following, the actuator 1 will be described as if it were a surgical instrument, that is, within an endoscope with a distal end and a proximal end. The distal direction in FIG. 1 is to the right, and the proximal direction is to the left.

Arranged radially outside of a tube 2 is a stator 10 which has two ring magnets 12, 14 that are axially magnetized in opposite directions so that the south pole of the magnets oppose each other in FIG. 1. When integrated in an endoscope, the ring magnet 12 is a distal ring magnet, and the ring magnet 14 is a proximal ring magnet.

A cylindrical coil 16 is symmetrically arranged between the ring magnets 12 and 14, wherein an also cylindrical back-iron element 18 consisting of a soft magnetic material is also arranged radially to the outside of the coil 16 and abuts the ring magnets 12, 14 flush radially to the outside. The back-iron element 18 terminates distally in a distal stator pole shoe 20 and proximally in a proximal stator pole shoe 22. The back-iron element 18 and stator pole shoes 20, 22 can be formed as a single part or from different parts that are all soft magnetic. The distal and proximal pole shoes 20, 22 are arranged between the coil 16 and the distal and proximal ring magnets 12, 14. Overall, this yields a flush, terminal surface radially to the outside. The stator 10 according to FIG. 1 is symmetrical across a plane of symmetry 24 in an axial direction.

Radially to the inside of the tube 2, the actuator 1 according to FIG. 1 has a rotor 30 that can consist entirely of a soft magnetic material. This rotor 30 tapers in the middle and terminates at a distal rotor pole shoe 32 and a proximal rotor pole shoe 34, wherein the distal rotor pole shoe 32 basically lies opposite the distal stator pole shoe 20, and the proximal rotor pole shoe 34 basically lies opposite the proximal stator pole shoe 22. The rotor 30 tapers in the middle so that it leaves a gap 36 open to the tube 2. Since the rotor 31 only contacts the tube 2 with the inner surfaces of the pole shoes 32, 34, the friction is reduced on the one hand, and a non-tilting arrangement of the rotor 30 in the tube 2 is ensured on the other hand. The rotor 30 is symmetrical across a plane of symmetry 38 in the axial direction.

The distal and proximal movements of the rotor 30 are restricted by a distal stop 44 and a proximal stop 46, respectively. In contrast to the rotor 30 that is arranged so as to be axially movable within the tube 2, the stops 44, 46 are fixed in an axial direction.

FIG. 1 shows a situation in which the rotor 30 is held in a first position 6 by the permanent magnets 12, 14 in which the rotor 30 abuts the proximal stop 46. The second position would be the one in which the rotor 30 abuts the distal stop 44.

If a change in the position of the rotor 30 is desired from the first position 6 into the second position 8, current is supplied to the coil 16, and the magnetic field electromagnetically generated by the coil 16 passes through the back-iron element 18 and the stator pole shoes 20, 22, as well as through the tube 2 into the pole shoes 32, 34 of the rotor 30, as well as to the permanent magnetic fields of the ring permanent magnets 12, 14. In this case, this magnetic field generated by the coil 16 is oriented such that it supports the magnetic field generated by the ring magnet 14 and counteracts the magnetic field generated by the ring magnet 12. Since the geometry of the proximal rotor pole shoe 34 depicted in FIG. 1 completely covers the proximal stator pole shoe 22, a very efficient magnetic flux is realized in this case, and a strong switching force is exerted on the rotor 30. At the same time, the holding force exerted by the distal ring magnet 12 is reduced. After switching, i.e., after the rotor 30 reaches the second position 8, the supply of current to the coil 16 is interrupted, and it accepts the holding force of the permanent magnetic field of the ring magnet 14.

The bistable electromagnetic actuator has ring magnets 12 and 14 that can comprise hard magnetic particles which are embedded in a plastic matrix. This allows the production of the ring permanent magnets to be very easy, economical and basically identical. In the embodiment according to FIG. 1, an opening, or respectively passage 40, is schematically indicated in the proximal ring permanent magnet, or respectively proximal ring magnet 14, through which a coil wire 42 is guided to the coil 16. Correspondingly for reasons of symmetry, the distal ring magnets 12 can also have a corresponding opening or passage 40 that, however, is not shown. This opening, or respectively passage 40, can be arranged at a location in the ring magnet 12, or respectively 14, such that the symmetry across the axis 4 is interrupted with regard to the opening, or respectively passage 40. In addition, the proximal stator pole shoe 22 in the exemplary embodiment according to FIG. 1 also has a corresponding penetration 40 through which the coil wire 42 is guided. This can keep the diameter of the bistable electromagnetic actuator very small, and the coil wire 42 is furthermore guided protected from the coil.

Figure 2:
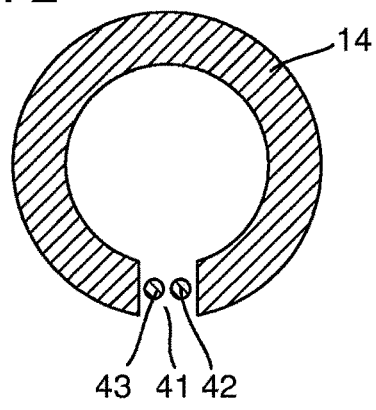
FIG. 2 illustrates a schematic sectional representation of a ring permanent magnet.

FIG. 2 schematically portrays a sectional view of a proximal ring magnet 14. An opening 41 is shown such that the ring magnet material is completely absent in one region. The coil wires 42 and 43 can then be guided through this region.

Figure 3:
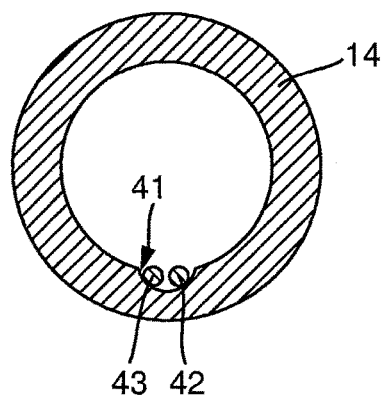
FIG. 3 illustrates a schematic representation of another ring permanent magnet.

FIG. 3 shows another schematic sectional representation of a ring magnet 14. The opening 41 is configured to be significantly smaller in this case. Magnetic material is still provided around the opening, although from the outside.

Figure 4:
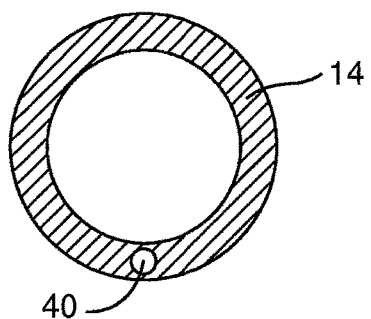
FIG. 4 illustrates yet another schematic sectional representation of a ring permanent magnet.

FIG. 4 shows another schematic sectional representation of a ring magnet 14 in which a passage 40 is provided. This passage can be provided while injection molding, or subsequently drilled. Both ring magnets 12 and 14 can be provided with equivalent openings 41, or respectively an equivalent passage 40. A corresponding passage or a corresponding opening 41 can also be provided in one or both stator pole shoes 20, 22.

In the production of ring magnets in an injection molding method comprising hard magnetic particles embedded in a plastic matrix, only a very small deviation in the size of the respective ring magnets is anticipated within one batch. Deviations as such can only arise from the shrinkage of the material after injection molding, wherein the shrinkage of one batch is substantially the same. In addition, the shrinkage of the mixture consisting of the plastic matrix and hard magnetic particles is reduced since there are also magnetic particles, and in principle, only the plastic matrix shrinks during hardening. Corresponding ring permanent magnets that consist of a plastic matrix and hard magnetic particles were produced which, for example, have an outer diameter of 2.26 mm, an inner diameter of 1.7 mm, and a width of 0.35 mm. Maximum deviations from magnet to magnet of 5 μm were found. With magnets that are exclusively produced from hard magnetic materials such as NdFeB or SmCo, the deviations are approximately 20 μm given correspondingly large ring magnets.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMBERS

1 Actuator
2 Tube
4 Central axis
6 First position
8 Second position
10 Stator
12 Distal ring magnet
14 Proximal ring magnet
16 Coil
18 Back-iron element
20 Distal stator pole shoe
22 Proximal stator pole shoe
24 Plane of symmetry of the stator
30 Rotor
32 Distal rotor pole shoe
34 Proximal rotor pole shoe
36 Gap
38 Plane of symmetry of the rotor
40 Passage
41 Opening
42, 43 Coil wire
44 Distal stop
46 Proximal stop

What is claimed is:

1. A bistable electromagnetic actuator comprising:
a tube;
a stator arranged outside of the tube; and
a rotor mounted in the tube so as to be displaceable along a longitudinal axis, the rotor at least partially comprises one or more of a paramagnetic and a ferromagnetic material and can be reversibly displaced between a first position and a second position by applying an electromagnetic field;
wherein the stator comprises two ring permanent magnets, a coil for producing the electromagnetic field, and a back-iron element having two stator pole shoes;
the two ring permanent magnets each having a cylindrical wall comprising hard magnetic particles that are embedded in a plastic matrix, the cylindrical wall defining an interior for holding the tube therein; and
each of the two ring permanent magnets having one of an opening or a passage formed in the cylindrical wall, the opening or passage passing through the cylindrical wall in a longitudinally axial direction to accept at least one coil wire of the coil in the opening or passage in one of the two ring permanent magnets.

2. The bistable electromagnetic actuator according to claim 1, wherein the ring permanent magnets are injection molded parts.

3. The bistable electromagnetic actuator according to claim 1, wherein at least one of the two stator pole shoes include an opening or passage penetrating in a longitudinally axial direction to accept the at least one coil wire of the coil.

4. The bistable electromagnetic actuator according to claim 1, wherein an outer diameter of the two ring permanent magnets is less than or equal to 5 mm.

5. The bistable electromagnetic actuator according to claim 1, wherein each of the two ring permanent magnets are arranged on one side of the coil.

6. The bistable electromagnetic actuator according to claim 1, wherein the back-iron element with the two stator pole shoes enclose the coil, and one of the two stator pole shoes are arranged on each side of the coil between the coil and a respective one of the two ring permanent magnets, wherein the rotor has two rotor pole shoes and one axial width of each of the two stator pole shoes is less than one axial width of each of the two rotor pole shoes.

7. The bistable electromagnetic actuator according to claim 6, wherein the axial width of each of the two stator pole shoes is less than an axial stroke of the actuator between the first position and the second position.

8. The bistable electromagnetic actuator according to claim 6, wherein the rotor with the two rotor pole shoes has an overall length in an axial direction that is greater than an outer distance between the two stator pole shoes in the axial direction.

9. The bistable electromagnetic actuator according to claim 1, wherein the rotor abuts a stop in one or more of the first and the second position.

10. The bistable electromagnetic actuator according to claim 1, wherein the two ring permanent magnets are oppositely axially poled.

11. A surgical instrument having a bistable electromagnetic actuator according to claim 1.

* * * * *